United States Patent [19]

Orrison, Jr.

[11] Patent Number: 4,938,233
[45] Date of Patent: Jul. 3, 1990

[54] RADIATION SHIELD
[75] Inventor: William W. Orrison, Jr., Albuquerque, N. Mex.
[73] Assignee: Techton, Inc., Albuquerque, N. Mex.
[21] Appl. No.: 80,958
[22] Filed: Aug. 3, 1987
[51] Int. Cl.$^5$ .............................................. A61B 6/10
[52] U.S. Cl. ..................... 128/849; 128/853; 128/156; 128/157; 252/478; 250/516.1; 250/519.1
[58] Field of Search ............... 128/132 R, 132 D, 156, 128/157, 849, 853; 264/122, 127; 252/478; 250/516.1, 517.1, 519.1, 515.1

[56] References Cited

U.S. PATENT DOCUMENTS

| | | | |
|---|---|---|---|
| 3,864,124 | 2/1975 | Breton et al. | 264/122 X |
| 3,901,829 | 8/1975 | Slingluff | 252/478 |
| 3,916,887 | 11/1975 | Kelly | 128/132 D |
| 3,948,295 | 4/1976 | Lemont et al. | 250/517.1 X |
| 4,123,392 | 10/1978 | Hall et al. | 252/478 |
| 4,194,040 | 3/1980 | Breton et al. | 264/127 X |
| 4,429,094 | 1/1984 | Massucco | 252/478 X |
| 4,437,013 | 3/1984 | Hondorp | 252/478 X |
| 4,558,093 | 12/1985 | Hatzenbuhler et al. | 128/132 R X |
| 4,601,286 | 7/1986 | Kaufman | 128/132 D |
| 4,604,998 | 8/1986 | Bellina | 128/132 D |
| 4,616,641 | 10/1986 | Teeple | 128/132 R |

FOREIGN PATENT DOCUMENTS

A0011085 of 0000 European Pat. Off. .
A0242227 of 0000 European Pat. Off. .
A2439460 of 0000 France .

Primary Examiner—Robert A. Hafer
Assistant Examiner—Kevin G. Rooney
Attorney, Agent, or Firm—Foley & Lardner

[57] ABSTRACT

A flexible shield for covering an article and attenuating the flux of electromagnetic radiation relative to the article includes a polymetric matrix charged with an attenuating filler. The shield has a transmission attenuation factor of at least 50% of a primary 100 kVp x-ray beam, a durometer of less than about 100 Shore "OO" and a coefficient of sliding friction relative to the article of at least 0.15.

27 Claims, 6 Drawing Sheets

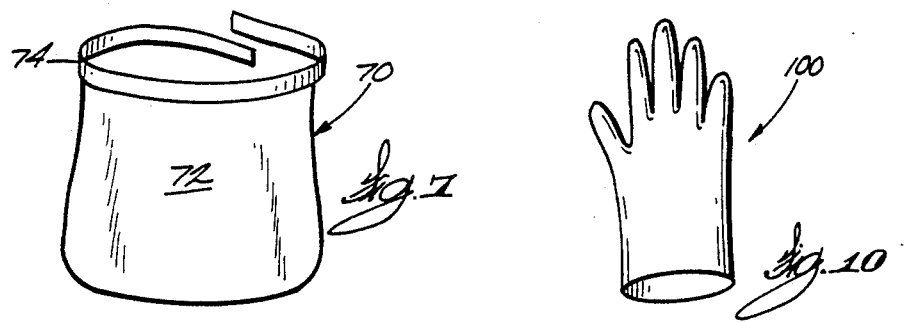
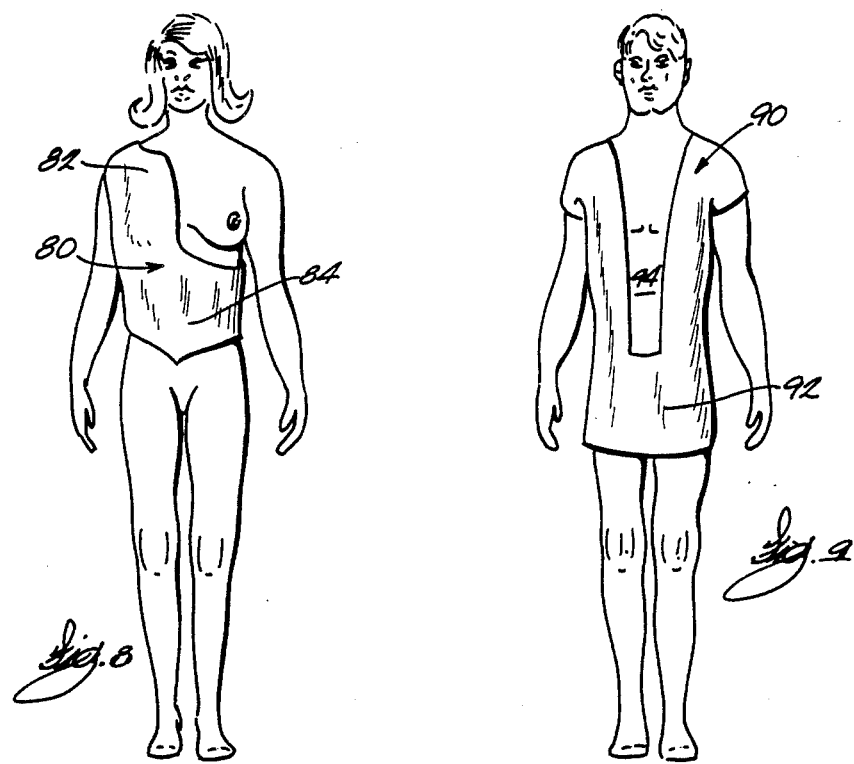
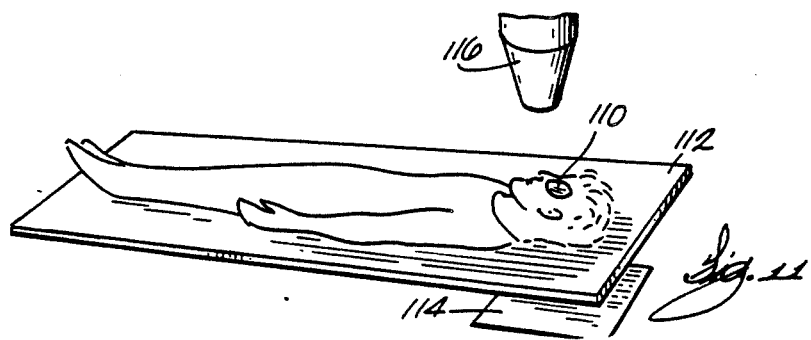

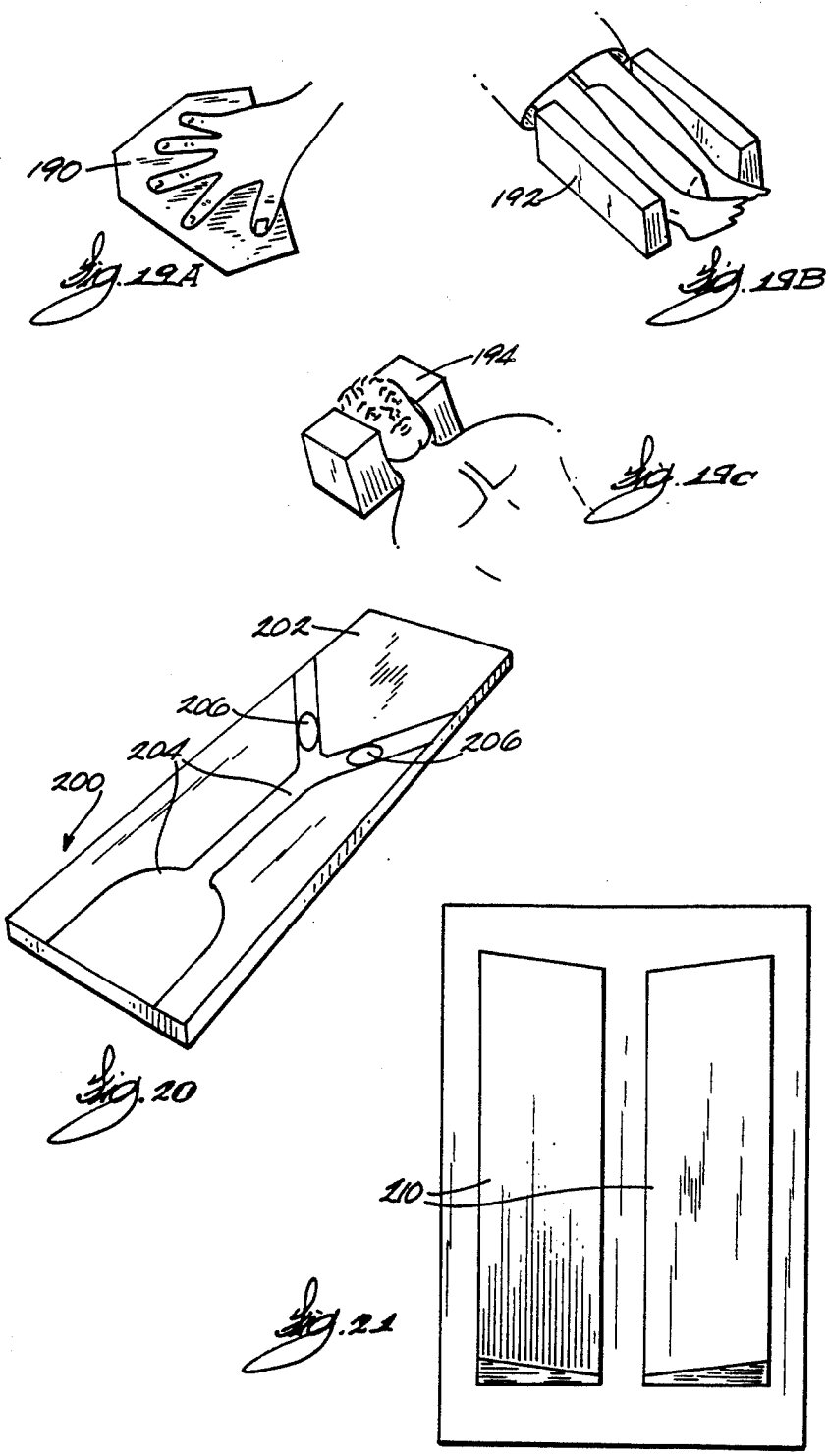

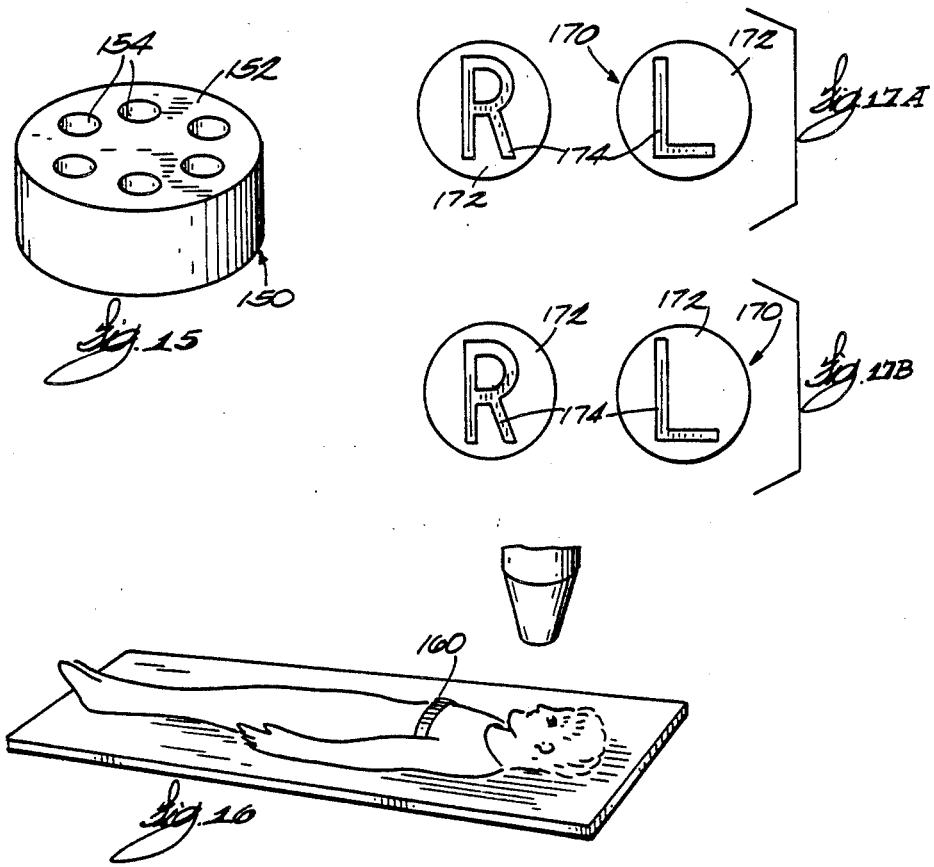
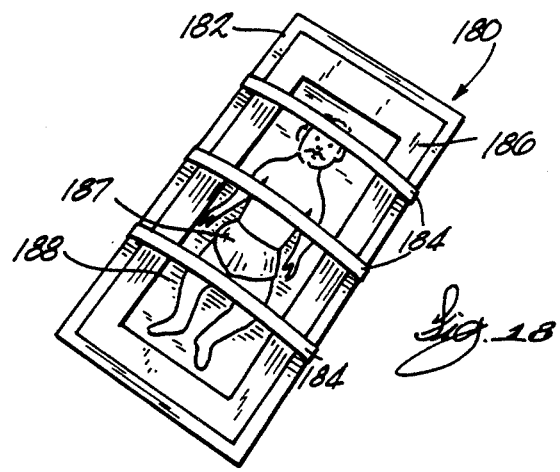

RADIATION SHIELD

TECHNICAL FIELD

The present invention relates, generally, to a radiation shield and, more especially, to a radiation shield for shrouding or otherwise covering an article or person and attenuating the flux of electromagnetic radiation across the shield relative to a radiation source. Thus, the radiation shield of the present invention is adaptable to such diverse applications as covering a patient and/or health care practitioner (or selected anatomical regions thereof) during a medical procedure or shielding a radiation such as a vial or canister of radionuclides. The shield of the present invention is particularly well adapted to provide radio attenuation over a wide range of the electromagnetic spectrum and may find incidental uses at very low or very high frequency extremes; more specifically, the shield of the present invention is particularly well suited for the attenuation of X and gamma rays, over the range generally bounded by the wavelength limits of $10^{-6}$ to about $10^{-10}$ centimeters. The shield of the present invention is designed for use in the field of medical radiology.

DESCRIPTION OF THE BACKGROUND ART

All manner and variety of situations require electromagnetic shielding. This is true over most of the electromagnetic spectrum, whether one considers radio wavelengths or gamma ray wavelengths or those in between. Particularly acute can be requirements for appropriate shielding of individuals from harmful or undesirable radiation such as that experienced in relationship to a wide array of medical procedures customarily encountered in the field of radiology. It is with particular reference to such endeavors that the ensuing description will be made; however, it will be appreciated by those skilled in the art that similar problems of shielding can arise in myriad other applications.

Radiology is a field growing at a substantial rate, both quantitatively and in terms of qualitative importance, having evolved to a high degree of sophistication over many years. Diagnostic procedures allowing non-invasive investigation of a patient, and specifically his internal anatomy, have been perfected to facilitate the determination of appropriate medical treatments. Radiology is also used extensively for medical therapy by selective irradiation of discrete anatomical regions of a patient, as may be encountered in certain forms of oncological treatment. Furthermore, and perhaps the area growing at the fastest rate, radiology is used as a tool in conducting various invasive procedures, such as the fluroscopic guidance and/or manipulation of instruments during surgical procedures. It is projected that all of these areas of radiology will continue to expand to the overall benefit of health care.

Radiology, relying upon x-radiation, is a powerful tool but one which requires carefully controlled safeguards. Living tissue is susceptible to damage through either prolonged or high intensity exposure. These are problems potentially suffered by patients and physicians or clinicians alike. For example, both the diagnostic and therapeutic applications of radiology typically require, and indeed are most beneficial when, only selected regions of the patient's anatomy are irradiated. Accordingly, the ability to isolate regions to be subjected to radiation and selectively shroud or protect regions beyond the contours or margin of the zone of interest are important goals to be achieved by the health care practitioner. Likewise, isolation of selected or desired anatomical regions during fluroscopic surgical techniques is of utmost importance, not only simply with regard to resolution but in light of the presence of the surgical team around the operating table, who need to be protected.

Shielding has become the paramount concern of those interested in controlling unwanted irradiation of regions of a patient's body or protecting medical personnel required to operate proximate an irradiated portion of a patient's body. These concerns regard two radiation sources: the primary x-ray beam which is utilized to irradiate the region of the patient's body required for the procedure and the scattered radiation which is an inherent attribute of the physics of electromagnetic energy traveling through and/or impinging on media of diverse density. It is noteworthy that scattered radiation is oftentimes more important a consideration of operating room personnel than primary beam radiation. Tight collimation provides a good measure of control over the initial path of the x-ray beam, however scattered radiation is ubiquitous about the operating table and cannot easily be controlled.

The historic approach to the control of undesirable radiation, primary or scattered, has been to shield patients and health care practitioners as reasonably required. Portions of a patient's body which ought not be irradiated are shrouded by radiopaque material; regions of a patient's body, and equally important, operating personnel subject to scattered radiation, are also shrouded or otherwise covered with attenuating material. Thus, it is not at all uncommon to find drapes fabricated from shielding material covering portions of a patient, mobile barriers comprised of radiopaque panels interposed between the patient and operating room personnel, and the use of protective apparel such as gloves, aprons, and the like including, in some instances, thyroid shields, lead glasses or even helmets, to provide adequate protection against scattered or stray radiation. The importance of such procedures cannot be underestimated since exposure tends to be cumulative and physicians or other health care personnel may be required to interrupt long-term scheduling in an operating room to provide sufficient time to allow ill effects of overexposure to abate before returning to that arena. Debilitating exposure also includes long-term effects such as radiation-induced arthritis and dermatitis.

The conventional approach to shielding has not changed significantly over many decades. Protective barriers or shields are conventionally fabricated from lead vinyl webs which are comprised of a sheet of vinyl polymer typical of the vinyl used in many apparel applications, loaded with a lead composition, typically a lead particulate in the form of either an oxide or a salt. Sheets or films ranging from about ¼ to 1 millimeter in thickness usually provide adequate shielding, considering simply the ability of such a shield to absorb or otherwise attenuate x-radiation. But, although clearly the material of choice for the entire recent history of this technology, lead vinyl sheeting has many inherent drawbacks. For example, the material is of only average pliability, at best. It takes permanent creases during normal handling and, when required for use in shielding, is not capable of draping smoothly over regions of a patient to be shrouded. Thus, typically, the lead vinyl sheeting will leave air pockets between it and the patient's body and, consequently, another interface at regions of differing density which tends to promote further scattering. Lead vinyl sheets are difficult to affix to or about a patient and/or the table which may be used for support; they are susceptible to slipping or moving in relationship to the patient during use, especially when configured as a surgical drape and used in a region of considerable activity during a surgical procedure. These shortcomings contribute to a lack of overall efficiency in use.

Lead vinyl sheet suffers other deficiencies apart from operational inadequacies. The product is not disposable or is the subject of disposal only at great inconvenience and cost due to the lead content of the article. That contributes, in turn, to attempts to reuse the product over many applications to maximize its useful life prior to the time of disposal, and this practice has many attendant difficulties. For example, lead vinyl sheet is not easily or adequately sterilized between uses and can harbor bacteriological or virus contamination which may be passed from patient to patient. This can be especially problematic in the event the shielding is configured for genital use.

In spite of the substantial shortcomings of lead vinyl sheet, it continues to receive considerable attention as efforts are made to improve shielding efficiency, particularly in an operating room. A large measure of such effort has concentrated on attempts to improve the application of conventional lead vinyl sheet, finding new configurations or placements of shielding vis-a-vis the scattering body in the primary beam. See, for example, Young et al., "Surface Shield: Device to Reduce Personal Radiation Exposure", 159 Radiology 801-803 (June 1986); Miller et al., "A Flexible Shield to Protect Personnel During Interventional Procedures", 155 Radiology 825 (June 1985). Thus, notwithstanding the known drawbacks and continual efforts to upgrade the shielding efficiency necessary in an operating room, the art has not adequately responded to date with the introduction of new materials specifically adapted for use in this environment.

SUMMARY OF THE INVENTION

The present invention responds specifically to the long-felt needs heretofore unmet by the prior art, and especially with a view to overcoming the inherent inadequacies of lead vinyl shielding webs. The shield of the present invention is flexible and compliant, providing a greater degree of patient comfort and safety as well as safety and convenience for health care personnel working in an x-ray environment. The shield of the present invention is disposable without requiring extraordinary precautions; being fully sterilizible prior to use, this feature permits disposable use to the benefit of both patient and physician by minimizing ancillary sources of contamination typically experienced due to multiple use.

The foregoing, and other advantages of the present invention, are realized in one aspect thereof in a flexible shield for shrouding or protecting an article or body, attenuating the flux of electromagnetic radiation to or from it, comprising a polymeric matrix charged with an attenuating filler; wherein the shield has a transmission attenuation factor of at least 50% of a primary 100 kVp x-ray beam, a durometer of less than about 100 Shore "00" and a coefficient of sliding friction relative to the article or patient of at least 0.15. Judicious materials selection provides shields within the foregoing parameters, for use over a wide range of applications, from transport protection for radionuclide materials, radionuclide shields and markers, film markers, or density wedges, on the one hand, through protective apparel for operating room personnel or patients such as thyroid shields, gonadal shields, diapers or protective aprons, or protective webs or drapes, on the other hand.

Thus, depending upon the specific utility to which the present invention is put, the shield envisioned herein preferably has a transmission attenuation factor of at least 75%, more preferably a transmission attenuation factor of at least 90%, and most preferably a transmission attenuation factor of at least 97%, all determined with reference to a 100 kVp x-ray beam. Transmission attenuation factors in respect of primary beam radiation are important, so too are those respecting a scattering attenuation factor, one exhibited by shields of the present invention of preferably at least 80%, more preferably at least 95%, and most preferably at least 97% as respects such a 100 kVp x-ray beam.

Durometer is a convenient measure of the drape and hand of a flexible shield in accordance with the present invention. Within the broad range recited above, the durometer is preferably in the range of from about 5 to about 80 Shore "00", and is most preferably in the range of from about 15 to about 40 Shore "00".

Stability of the shield of the present invention relative to the article or patient to be protected, or a table or other appliance associated with a desired procedure, may be tailored depending upon the application at hand. Measured as a coefficient of sliding friction as an indication of the placement stability of the instant shields, that coefficient (determined as the tangent of the angle of inclination to induce sliding) may be greater than 0.5, under certain circumstances is preferably greater than 0.75 or even greater than 1.0, and for specific applications such as a surgical drape or protective shield for direct contact with a patient, is preferably in excess of 2.0.

The flexible shield of the present invention is preferably comprised of a viscoelastic polymeric matrix charged with an attenuating inorganic filler. The matrix is comprised most preferably of a polymer selected from the group consisting of viscoelastic vinyl polymers or vinyl acetate copolymers, silicones and urethanes, although many other suitable compositions exist. Most preferred are the vinyl polymers or copolymers. The filler is preferably a particulate of an inorganic salt having a radiopaque cation, most preferably selected from the group consisting of barium, iodine and mixtures thereof, although many other suitable materials exist. Most preferred is a barium salt such as barium sulfate which is not toxic, relatively abundant in terms of commercial supply, effective as an attenuating filler (i.e., radioattenuant), and easily processed. In a highly preferred embodiment, regardless of the presence of any iodine salts, a tincture of iodine is compounded with the initial polymer. A highly preferred composition in this regard includes a matrix of a plasticized vinyl polymer wherein the ratio of plasticizer to polymer is in the range of from about 5:1 to about 32:1 and the filler is present in the range of up to about 80%, more preferably in the range of from about 10% to about 70% and most preferably in the range of from about 20% to about 60%, that filler being barium sulfate, with less than 0.5% tincture of iodine. Various fragrances may be added to the web.

Disposable radiological garments or other shields specifically adapted to be worn by or selectively draped about a patient constitute an important class of articles in accordance with the present invention. These include radiation protection pads, thyroid shields, male gonadal shields, female gonadal shields, diapers, protective aprons (including miniaprons), breast shields, scoliosis shields, protective gloves, protective eye disks, protective barriers, and infant stabilization/shield members. Such other articles as phantoms useful in replicating conditions for radiological studies, shields, markers, table pads and density wedges are important for related applications as well. Further along these lines, any of the foregoing articles are relatively easily trimmed to shape or fit to the extent necessary or desirable insofar as the flexible shields in accordance with the present invention may be cut with any convenient tool, such as scalpels or other instruments typically found in an operating room or in other hospital settings.

The products of the present invention, regardless of application to which the same are put, are easily fabricated in any shape simply by curing the matrix and captured particulate in a mold of suitable shape and dimension. Typically, the polymeric mix is compounded, along with any necessary stabilizers, thickening agents, surfactants or the like, particulate is blended and sufficiently worked to develop uniform distribution and the composition is cast and allowed to cure, set or polymerize as the case may be.

Compositions having the preferred constituents may be sterilized in any convenient manner, including either gas sterilization or irradiation sterilization; the latter being a particularly advantageous approach since the shields may be simultaneously subjected to quality control examination while being sterilized. An adequate shelf life is enjoyed by shields in accordance with the present invention, whereby the same may be stocked and removed from inventory for use as required. Utilizing the preferred barium sulfate filler as the radiopaque material, the shield may be disposed of as ordinary refuse without the need for specialized techniques.

Other advantages and a fuller appreciation of specific adaptations, compositional variations, and physical attributes will be gained upon an examination of the following detailed description of preferred embodiments, taken in conjunction with the figures of drawing.

BRIEF DESCRIPTION OF THE DRAWINGS

The drawings herein illustrate an array of products, all made in accordance with the present invention, wherein:

FIG. 7 is a side elevation view of a miniapron which, unlike those aprons of FIG. 6, is designed for only partial as opposed to full torso protection;

FIG. 8 is an anterior view of a female patient, shown wearing a breast shield;

FIG. 9 is an anterior view of a male patient wearing a scoliosis shield;

FIG. 10 is a plan view of a protective glove;

FIG. 11 is a perspective view of a patient undergoing radiological treatment about the patient's head and neck, which patient is shown wearing a protective eye disc;

FIG. 15 is a perspective view of a radionuclide transportation and/or storage device;

FIG. 16 is a perspective view of a patient undergoing radiation treatment and/or examination, wearing a marker;

FIGS. 17A and 17B are plan views of film markers;

FIG. 18 is a top plan view of an infant stabilization device incorporating protective radiation shields;

FIGS. 19A, 19B and 19C illustrate a variety of patient positioning devices;

FIG. 20 is a perspective view of a fluoroscopy table pad, in this configuration one adapted for angiography; and FIG. 21 is a top plan view of density wedges.

DETAILED DESCRIPTION OF THE INVENTION

Figure 1:
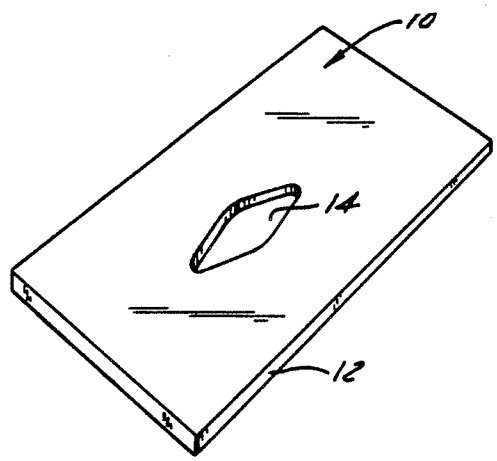
FIG. 1 is a perspective view of a radiation protection pad.

The present invention relates broadly to flexible shields for attenuating the flux of electromagnetic radiation over a broad wavelength range. However, the shield of the present invention is most particularly adapted for use in x-ray shielding such as that encountered or necessary in respect of the shielding of patients during various radiological procedures, the shielding of health care personnel during such procedures or even the shielding of sources of x- or gamma radiation to protect individuals or articles from unwanted exposure. Accordingly, the present invention will now be described in detail with respect to such fields of endeavor; however, those skilled in the art will appreciate that such a description of the invention is meant to be exemplary only and should not be viewed as limitative on the full scope thereof.

The shields of the present invention are characterized by an ability to attenuate radiation while possessing a hand and drape rendering the same highly conformable to the article or body to be shielded and highly comfortable to a wearer. These attributes are achieved through a particular composition meeting a special combination of physical parameters.

The shield of the present invention is based upon a polymeric matrix and an attenuating filler. The polymeric matrix is preferably a viscoelastic material such as a viscoelastic vinyl polymer, vinyl-acetate copolymer, silicone or urethane. A highly preferred viscoelastic polymer is one such as that disclosed in U.S. Pat. No. 4,621,808, incorporated herein by reference and relied upon. That composition is a highly plasticized polyvinyl chloride wherein the ratio of plasticizer to resin may vary broadly over the range of from about 5:1 to about 32:1. Preferred plasticizers include dialkyl phthalate, diundecyl phthalate, dioctyl phthalate and duisononyl phthalate. Thixotropic thickening agents, stabilizers, enhancers and surfactants may also (optionally) be included as set forth more particularly in the '808 patent. The resultant material is one having suitable characteristics for use as the polymeric matrix in accordance with the present invention. Alternatively, a similar composition, but based on a vinyl-acetate copolymer, may be adapted to the same end with additional benefits to be mentioned hereinbelow.

Other polymeric matrices useful in accordance with the present invention include silicones and urethanes (polyester, polyether and polybutadiene-based), rubbers (both natural and synthetic) as well as various gels. Examples of compositions which may be tailored to use in compounding shields in accordance with the present invention include those disclosed in U.S. Pat. Nos. 3,419,006 and 3,935,099. Yet other compositions of potential interest include polystyrene butadiene block copolymers, (low density) polyethylene, poly (n-butyl methacrylate), polystyrene diluted with tricresyl phosphate, poly (methyl acrylate), poly (n-butyl methacrylate), and various polystyrenes and polyiosprenes, poly (alpha-methylstrene) or the gels including polyacrylonitrides, cellulose trinitrate, or poly (vinyl chloride) in di-2-ethylhexyl phthalate, cellulose tributyrate, cellulose nitrate and gelatin, or cross-linked gels such as poly (beta-hydroxy ethylmethacrylate), provided the same possess the requisite durometer and friction charateristics described herein. Various water based gels (hydrogels) including those prepared with starch, polyacrylonitrile, polyethylene oxide, polyvinylpyrolidone, hydrophilic urethanes, etc. may also be used. Those skilled in the art, guided by the descriptions set forth herein, may select other suitable matrix materials meeting the functional attributes required for use in the present invention and, thus, the foregoing listing is simply representative of adequate candidates of the polymer matrix used in shields made in accordance with the present invention.

The attenuating filler may be any composition compatible with the matrix, which exhibits radiopacity to the electromagnetic radiation of interest: Radioattenuants include compositions comprised of barium, bismuth, iodine, uranium and zirconium containing compositions, such as salts or oxides thereof, singly or in combination. For purposes of the x-ray shields in accordance with the present invention, the attenuating filler is most preferably a particulate barium sulfate which has the added advantage of being non-toxic, although certain bismuth compounds are also regarded as neither toxic nor carcinogenic.

The composition disclosed and claimed in the '808 patent mentioned above includes a barium sulfate constituent to develop a weight useful in an exercise program. The compositions necessary to provide a weight, however, include barium sulfate additions typically considerably in excess of those envisioned as necessary or desirable when that filler is utilized in forming a shield in accordance with the present invention. In the present case, the barium sulfate attenuant is present in the shield in the range of up to about 80%, preferably from about 10% to about 70%, and most preferably in the range of about 20% to about 60%. Thus, considering the attenuating characteristics of the shield, in a usable thickness range of from about 2 mm to about 1.5 cm, it has a transmission attenuation factor relative to a primary 100 kVp x-ray, of at least 50%, preferably at least 75%, more preferably at least 90%, and most preferably at least about 97%. That same shield, when examined respecting the scattering attenuation factor, exhibits a factor of at least 80%, preferably at least 95%, and most preferably about at least 97%.

EXAMPLE

A series of test webs were prepared to examine into scattering attenuation effectiveness of differing compositions and thicknesses. Each web was made from a viscoelastic polymer exemplified in U.S. Pat. No. 4,621,808, loaded with incrementally varying charges of barium sulfate. Webs of varying thickness were cast and, upon curing, were exposed to scatter from a 100 kVp x-ray beam. The results are reported in the Table below.

TABLE

| $BaSO_4$ (%) | Thickness (mm) | Scatter Attenuation (%) |
| --- | --- | --- |
| 10 | 2 | 59 |
| 10 | 5 | 71 |
| 25 | 2 | 70 |
| 25 | 4 | 80 |
| 25 | 6 | 83 |
| 50 | 2 | 78 |
| 50 | 4 | 90 |
| 50 | 6 | 96 |
| 75 | 2 | 83 |
| 75 | 4 | 95 |
| 75 | 6 | 98 |

An additional test was performed to ascertain a primary beam attenuation threshold. It was determined that a 5 mm web having a 75% $BaSO_4$ content attenuates 97% of the primary of a 100 kVp x-ray beam.

Recognizing that the matrix material itself contributes at least slightly to attenuation, those skilled in the art can readily extrapolate at least general information respecting the interrelationships among barium content, web thickness and attenuation factors. Guided by the principles herein, radiation shields of suitable size and composition can then be tailored to meet the demands of a given application.

Conventional lead vinyl shielding is capable of providing attenuation factors of the same order as the attenuation factors mentioned above and, indeed, in thinner sheets than required by the shield of the present invention. However, important attributes of the instant shield, distinguishing it from conventional approaches, concern both the conformability and stability thereof when in use. These attributes are related to the physical properties of durometer and coefficient of sliding friction of radiation shields of the present invention.

The preferred compositions for the viscoelastic matrix of the present invention, and especially the plasticized vinyl compositions, have a drape and hand which materially improve the utility of shields of the present invention when used as radiological garments or protective shielding members. Likewise, protective shields for protection of radionuclides during transport are of vastly improved character over conventional shields. These advantages are partly attributable to the durometer of the material. It is preferred that the durometer of the shield or protective member be less than 100 Shore "00" as measured on a Shore durometer, Shore Manufacturing Company, Jamaica, N.Y. More preferably, the softness should fall in the range of from about 5 to about 80 Shore "00", most preferably in the range of from about 15 to about 40 Shore "00". The selection of material to yield an appropriate softness (which manifests itself in terms of hand and drape viewed in the apparel context) provides a material which is highly conformable to the body or article being shrouded. This is an important consideration, being highly advantageous when the shield is used for radiological procedures and is applied to a patient. Unlike conventional lead vinyl sheeting which permits the formation of, or sometimes even creates, pockets or voids and resulting air-gaps between the patient's body and the shield, a shield in accordance with the present invention conforms to depressions or undulations and, in the preferred compositional implementation, closely approximates the anatomy of the patient, lying contiguous with the skin. These preferred materials exhibit the characteristics of creep, and thus, shields of the present invention will tend to "flow" to fill spaces, a factor contributing to comfort and efficiency in use.

Another physical attribute which improves functional operability of shields of the present invention regards the physical parameter of coefficient of friction, in this case sliding friction. The preferred materials, the vinyl polymers, and especially vinyl-acetate copolymers, insure a coefficient of friction relative to the article to be shrouded or the patient's body to be shielded sufficient to maximize the placement stability of the shield when in use. The highly preferred composition, as noted above relative to the '808 patent, is particularly preferred for that reason and even more so when the vinyl-acetate copolymer is employed. In these cases, the surface of the shield is slightly tacky, a feature enhanced by the acetate in the embodiment employing the copolymer. Regardless, the shield, when applied to a patient's body or an article (e.g., a table), not only conforms closely with any topical irregularities but has a sufficiently high coefficient of friction that it cannot be easily dislodged or moved. Indeed, in thicker sections, the shield is best removed by peeling as opposed to sliding. It will be apparent to those skilled in the art that such a high degree of tenacity is not required in all embodiments or for all practical applications but is a parameter available for optimizing the utility of shields of the present invention. Along these lines, the shield of the present invention possesses a coefficient of sliding friction relative to the article or body being shielded of at least 0.15, preferably greater than 0.5, more preferably a coefficient greater than 0.75, still more preferably a coefficient greater than 1.0, and in highly preferred embodiments, a coefficient of sliding friction in excess of 2. The shielding material of previous choice, lead vinyl sheet, has a much lower coefficient of friction and, as noted above, tends to be dislodged quite easily from a patient's body; it is relatively smooth and slips easily from harder objects such as tables or containers housing radionuclide materials.

A further important feature of the shield of the present invention, and particularly remarkable when configured as a protective member for use in radiological procedures, is its elastic properties. The shield is formulated in a preferred embodiment to possess elastic hysteresis. More particularly, it is preferred that the shield of the present invention exhibits elastic hysteresis over a strain range in excess of 150%. Depending on the composition elected and the strain rate chosen, hysteresis may be observed over an even greater range with but minor permanent set. Set is a difficult parameter to measure with exactness in the preferred embodiments wherein the shield has a high coefficient of friction since it tends to return to its original shape only slowly and, depending upon the rate of strain, may be distended permanently over substantial ranges of elongation. For example, depending upon the rate of strain, elongations of 150% to about 600% without failure may be observed. This is related to the tensile strength of the preferred compositions, which can range from about 150 to about 800 psi. Suffice it to say, that for practical applications, a hysteresis over strain range in excess of 150% without substantial permanent set, if any set at all, is a typical observation.

Shields (and especially radiological garments or protective materials made therefrom) in accordance with the present invention exhibit materially improved characteristics when compared with the historic material of choice for such shields, lead vinyl sheeting. As noted above, the shields of the present invention are equally effective in blocking both primary beam radiation and scattered radiation. Yet, they are more comfortable to both patient and physician in use and more convenient in respect of the conformability and stability of the shielding during surgical procedures.

Disposability is an additional and important characteristic of the shields of the present invention when adapted for contact with patients. Lead vinyl sheet can be sterilized only imperfectly and can house both bacteriological and virus contamination which may be passed from patient to patient notwithstanding diligent efforts to sterilize the material between uses. The shield of the present invention, particularly when compounded in accordance with the preferred materials, is specifically destined for single or disposable use applications. It is of relatively low prime cost, thus eliminating financial penalty from the one-time utilization for which it is designed.

The material is susceptible of convenient sterilization using conventional techniques, such as gas sterilization or sterilization by radiation. When sterilized by radiation, the procedure is also useful in performing quality control. For example, homogeneous distribution of attenuating material is a quality control objective which may be tested as can the threshold transmissibility of a shield made in accordance with the present invention. Appropriate detectors may be located along the manufacturing line to detect levels of radiation passing through the shielding material while it is being subjected to sterilization via radiation. In the event thresholds are exceeded, either in respect of the overall shield or in respect of localized regions thereof, the shield may be rejected, manually or automatically, for failure to meet appropriate criteria.

Disposability is also enhanced when the highly preferred compositions are employed, particularly utilizing barium sulfate as the attenuating material, since the same are not toxic and require no specialized procedures for disposal. This is an important distinction over lead-containing shields.

The preferred materials for fabricating radiation shields in accordance with the present invention may be configured in any number of convenient shapes. The composition may be molded or cast to shape and, once set, may be easily cut as required to provide articles specifically tailored for particular applications. Net or mesh webs of proper shapes and sizes may be impregnated with the composite matrix/filler which sets to shape to yield a desired article. Exemplary articles or radiation shield products in accordance with the invention are illustrated in FIGS. 1-21 to demonstrate an array of useful articles, to which drawing reference is next made.

FIG. 1 illustrates a radiation protection pad in accordance with the present invention, designated generally as 10. The pad 10 is comprised of a web designated generally as 12, here shown in the form of a rectilinear slab. Pads such as the radiation protection pad 10 are typically placed over an area of a patient to be examined with a central, preferably tapered aperture 14 defining the region within which the examiner will be working on the patient. That center cut or aperture 14 also will be placed coincident with the primary x-ray beam. The tapering is generally preferred, especially in the protection pad 10 of the present invention, to present a convenient field within which to work and to provide an edge which will reside closely in contact with the patient's body. The radiation attenuating material from which the web is made will adequately protect the physician as he works on the patient. A typical thickness for the pad 10 is on the order of about one centimeter when preferred compositions are utilized, that being considered effective for radiation encountered as the result of a 100 kVp x-ray primary beam. Such shields take on prime importance in the protection of a physician's hands when working close to a primary x-ray beam, preventing such debilitating or untoward effects as the development of radiation-induced arthritis, dermatitis or hair loss. This can be as important a consideration in whether the radiation be that associated with a mammography, having a primary beam perhaps less than 20 kVp as is for high energy, high resolution work with beams over 120 kVp. Shields of the present invention can be tailored for remarkably effective use throughout this energy range and are conveniently adaptable for use beyond it.

Figure 2:
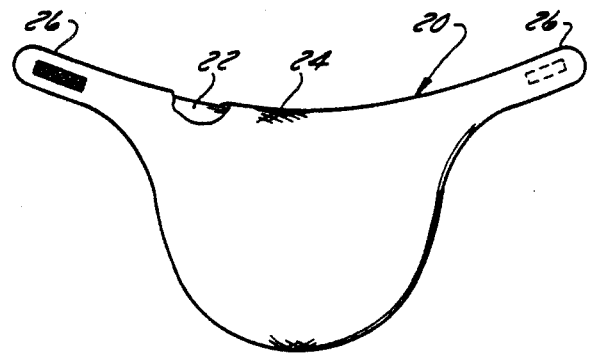
FIG. 2 is a plan view of a thyroid shield.

FIG. 2 illustrates a thyroid shield, designated generally as 20. It is comprised of a body of radiation attenuating material 22 bearing a cloth covering 24 to improve comfort. The thyroid shield, as is conventional, includes opposed ends 26 which, preferably, bear an attachment member, such as that known as Velcro, to facilitate attachment of the thyroid shield to the physician.

Figure 3:
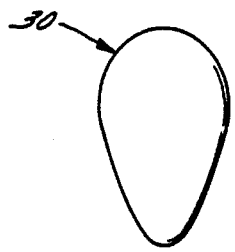
FIG. 3 is a plan view of male gonadal shield.
Figure 4:
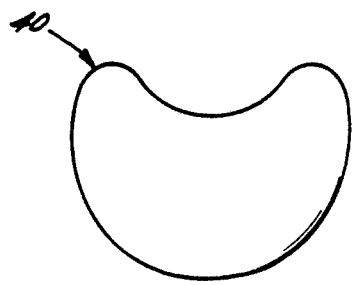
FIG. 4 is a plan view of a female gonadal shield.

FIGS. 3 and 4 illustrate male and female gonadal shields 30 and 40, respectively. As the name aptly tends to imply, these shields are configured to protect the gonadal region of a patient during a radiological procedure. Highly important in this regard is the sterile nature of such a shield which, optimally, is a single use or disposable article which is disposed of following use to avoid transferring biological contaminants from one patient to another. In the preferred embodiment of the present invention, both the polymeric matrix and barium sulfate attenuant may be disposed of in the ordinary course, without undertaking special treatments or precautions as is the case with lead-containing materials. Accordingly, the combination of ease of sterilization at the outset and disposibility once used, commends the present invention for specific use as gonadal shields as illustrated in FIGS. 3 and 4.

Figure 5:
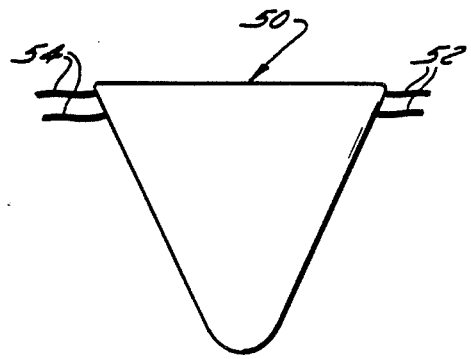
FIG. 5 is a plan view of a diaper.

FIG. 5 is a view of a diaper designated generally as 50 having attachment means 52 and 54 at opposed upper edges to facilitate the disposition of such a diaper about a patient. Diapers 50 may be made in a range of sizes to fit adult or adolescent patients as well as infants, to protect the gonadal and abdominal regions of the patient during a radiological procedure.

Figure 6A:
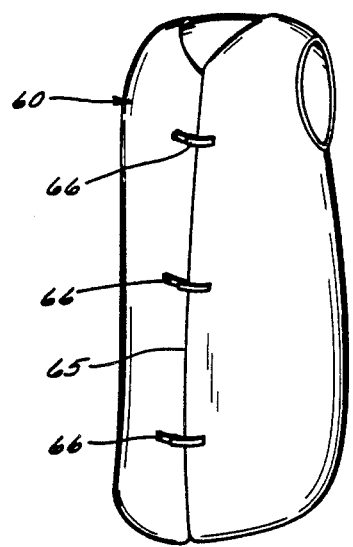
FIGS. 6A and 6B are perspective views of protective aprons, a wrap around and front shield apron, respectively.
Figure 6B:
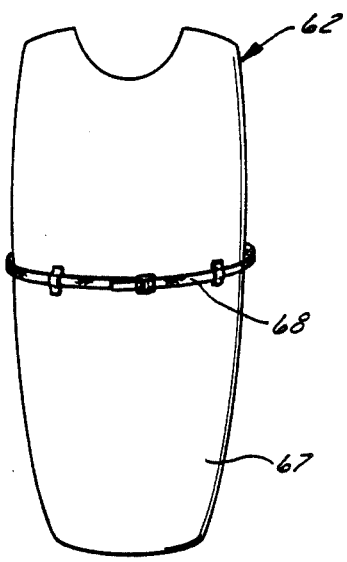

FIGS. 6A and 6B show full torso protective aprons designated generally as 60 and 62, respectively. The torso apron 60 is comprised of an enveloping shroud 64 which encircles the wearer's body, front and back. Opposed marginal edges meet at a juncture 65 which is secured by means of fasteners 66. If desired, the body of the apron 64 may be covered with cloth or a cloth-like material to improve wearer comfort and facilitate the placement and securement of the fasteners 66. The apron 62 is different, especially insofar as its body panel 67 drapes only the frontal portion of the wearer. In this instance, the apron 62 does not surround the torso in the manner of the apron 60. It is secured to the wearer by ties or straps 68 encircling the waist region.

A miniapron 70 is shown in FIG. 7. It is comprised of a body or panel region 72 suspended from the waist of a wearer by ties or a fastening member 74. This apron covers only a portion of the lower torso of the wearer, unlike the apron 62 mentioned above. Regardless, however, each of the apron designs of FIGS. 6 and 7 is configured to provide both examiner/patient comfort and examiner/patient safety in connection with radiological procedures or other exposure to sources of radiation, especially x-ray and gamma ray radiation consistent with the principal thrust of the present invention.

FIG. 8 illustrates a breast shield designated generally as 80 worn by a female patient, for example during a mammographic x-ray procedure. The breast shield 80 is thus comprised of an upper shield 82 which protects the portion of the patient's anatomy which is not subjected to examination, the shield 82 extending downwardly of the patient's body from her shoulder toward the abdomen. A further shielding element 84 is provided about the gonadal region of the patient to protect those organs as well. Accordingly, only the area to be examined is presented for irradiation while surrounding regions are protected against unwanted exposure.

FIG. 9 shows a scoliosis shield, designated generally as 90. This shield is comprised of radiation attenuating material cut into a configuration conventional for such shields, allowing it to drape from the shoulder region of the patient to the lower abdomen. The shield 90 further includes a gonadal shield 92. The scoliosis shield, as is generally conventional, leaves an exposed region 94 for examination.

FIG. 10 shows a protective glove designated generally as 100 fabricated from radiation shielding material in accordance with the present invention. Alternatively, the glove may be mesh impregnated with uncured matrix material having compounded therein an appropriate charge of attenuant, such as barium sulfate. The charged matrix is subsequently permitted to set and form the desired glove. Regardless of the method of manufacture, the glove may be used by a health care practitioner when manipulating instruments or tools proximate a primary beam or in a region of secondary or scattered radiation; it may be worn by a patient to protect his or her hand during examination of the patient's body in regions next to such a radiation source; or the glove may be worn by an individual who is required to handle sources of radioactive material. In any of these events, or other uses as may be envisioned by those of ordinary skill in the art, the flexibility of the preferred compositions in accordance with the present invention permit greater dexterity on the part of the wearer than may be realized by stiffer materials from which such gloves may be fabricated.

FIG. 11 is a perspective view of a patient wearing a protective eye disc 110 in accordance with the present invention. The patient is shown supported on an examination table 112 above a photographic plate 114, positioned for irradiation by an x-ray tube 116 to provide an x-ray image of the patient's head and/or neck region. In this instance, eye protection can be especially important to safeguard the patient's optical anatomy from unwanted or undesirable exposure to the primary beam. There are other situations in which protective eye discs of this sort are particularly useful, even outside the range of wavelengths for which this invention is broadly developed. More specifically, so-called "tanning rooms" have become quite popular for individuals to tan their skin under artificial light conditions. It is recommended and commonplace that eye protection be worn, particularly where UV (ultraviolet) lights are employed in the tanning process. Eye protection devices are sometimes shared amongst individuals, notwithstanding the ease of transmission of eye disease. Thus, disposable eye protection discs in accordance with the present invention will find additional use in that environment notwithstanding the fact that the wavelength of radiation is shorter than the x-ray band.

Figure 12:
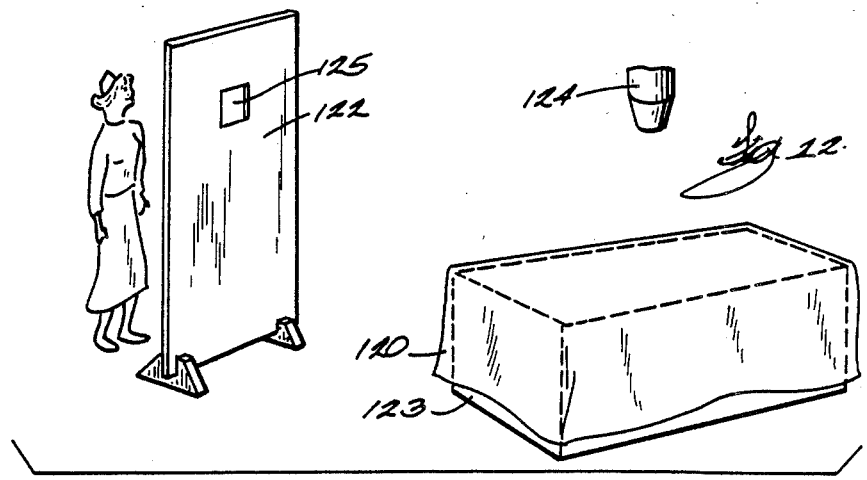
FIG. 12 is a perspective view illustrating a protective barrier.

FIG. 12 illustrates an array of protective barriers 120 and 122 used to protect personnel in an x-ray examination room or the like. In this instance, the protective barrier 120 is associated with an examination table 123 placed beneath the tube of an x-ray machine 124. When a patient is examined on the table 123, scattered radiation from beneath the table is confined by the drape or shield 120. The shield 120 may envelop the entirety of the examination table 123 or be placed only on the side or sides toward which the examining attendant faces. That attendant, as also shown in FIG. 12, is protected by the shield or protective barrier 122 as well. In this case, the shield is formed with a cut-out or visually transparent component 125 through which the examiner may observe the patient. Although a certain amount of radiation may be transmitted through the region 125, the vast majority of scattered radiation will be absorbed by the protective barriers.

Barriers of the sort shown in FIG. 12 can be of material assistance in establishing either remote or temporary x-ray facilities. Most x-ray rooms include lead lining in or on the walls to confine radiation and prevent stray radiation from leaving the region of the x-ray apparatus. It is not always convenient or desirable to provide that type of lead-circumscribed environment, in which case protective barriers made in accordance with the preferred compositions of the present invention are capable of providing temporary but nonetheless highly efficient shielding.

Figure 13A:
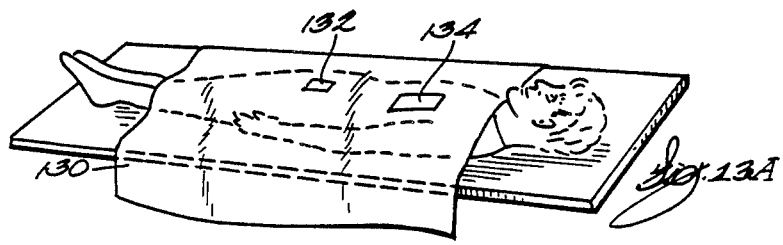
FIGS. 13A and 13B illustrate a protective drape, showing the same disposed over a patient in preparation for a cardiac catheterization procedure.
Figure 13B:
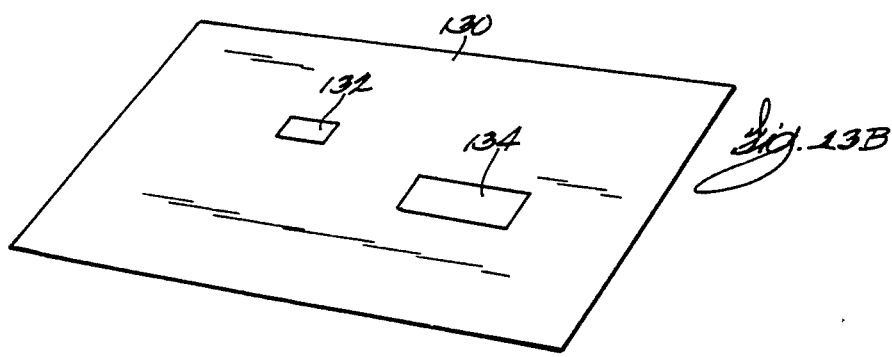

FIGS. 13A and 13B show a protective drape, in this instance configured for a cardiac catherization procedure to be performed on a patient. The drape, designated generally as 130, is sized to cover the patient essentially over the majority of his body, being draped from the upper chest region to the lower legs as best viewed in FIG. 13A. It is also preferred that the drape be of sufficient width to span entirely across the patient and the operating table, likewise as shown. The drape 130 is fabricated from radiation shield material in accordance with the present invention. A first keyway or cut-out 132 is formed in the upper thigh region while a panel or window of neutral material 134 is provided in the drape in the region of the patient's heart. The cut-out provides the physician with an entry point to insert a needle or through which to introduce the catheter instrumentation. The patient is subjected to x-ray radiation passing through the region of the neutral window 134. Watching an appropriate display responsive to that radiation, the physician may manipulate the catheter from the region of cut-out 132 into proper position proximate the heart. During that procedure, however, the protective drape 130 protects operating room personnel from scattered radiation.

The drape 130 is further noteworthy for two additional reasons. The compliancy of the drape 130 allows it to reside closely next to the patient's body. It is comfortable and fits positively against the undulating surface of the patient, thus improving its stability while the surgical team is operating on the patient's body. The coefficient of friction between the drape and the patient's skin adds to that stability, preventing movement of the drape during the surgical procedure and further obviating the need to take extraordinary measures to prevent slippage or movement of the drape as is sometimes required with drape materials which fail to exhibit these attributes.

Figure 14A:
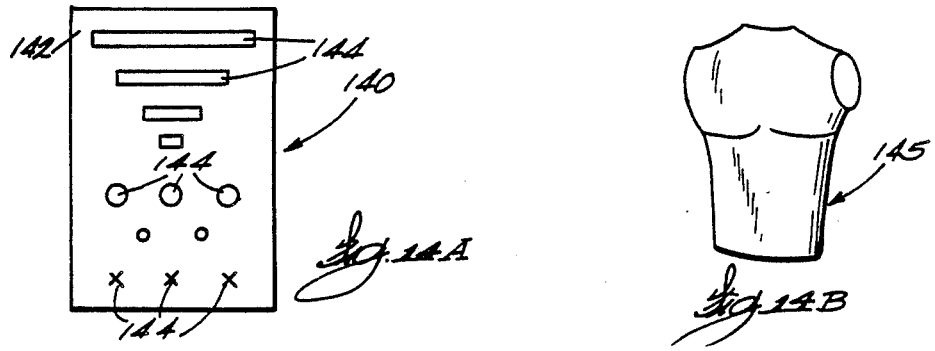
FIGS. 14A and 14B are plan views of phantoms, the former showing a test pattern for quality control purposes and the latter an anatomy phantom.
Figure 14B:
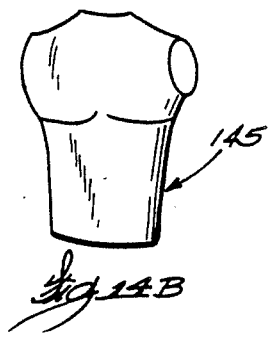

FIGS. 14A and 14B represent phantoms which are used to simulate or replicate desired conditions, e.g., for quality control testing of x-ray apparatus. In the case of the phantom shown in FIG. 14A, designated generally as 140, a rectilinear web 142 includes an array of differing density elements of differing shapes, identified generally as 144. In some instances, it is the web 142 which is fabricated from attenuating material in accordance with the present invention whereas the indicia 144 will be cut out from the substance of that web; in other instances, the web 142 may simply be a supporting structure on which is borne indicia 144 made from the radiation attenuating material fabricated in accordance with this invention. In either of such events, however, irradiation of the phantom 140 will yield patterns to be seen on a detector or to be exposed in a sensitive photographic emulsion, ultimately to examine the operational characteristics of the x-ray apparatus itself. The phantom shown in FIG. 14B, designated generally as 145, differs from that noted above, insofar as this is in the form of an anatomical phantom. Such a phantom may be in the nature of a pedagogical aid and, in that regard, may or may not include elements of pathology to be detected by a student or someone undergoing an examination; perhaps it is used to ascertain the resolution of the x-ray equipment. In any event, phantoms of this sort have long been used, but in the present case the ability to alter compositions and provide electromagnetic radiation-sensitive gradients vastly improves one's ability to tailor phantoms to provide broader range of desired results.

FIG. 15 shows a radionuclide transportation and storage device, designated generally as 150. In this instance, the article 150 is comprised of a body of radiation attenuating material 152 having a plurality of blind apertures 154 formed therein. Each of the apertures 154 is dimensioned to receive a vial of radioactive material to be transported and/or stored, for example material used in radiation treatment in a hospital. To date, a conventional approach in transportation and storage of radionuclide material is to pack vials in cotton housed within lead containers. There are obvious shortcomings to such a procedure. Given the nature of the composition of the present invention and the facility with which is may be fabricated into shape, each of the blind apertures 154 may be slightly undersized to ensure a close interference fit between the body 152 and the vials to be inserted in those apertures. Once in place, a cover of similar material may be disposed over the article 150 and secured in any convenient manner for transport and/or storage. In the event of an accident, the radiation attenuating material which safeguards personnel from radiation will also advantageously cushion the vials containing the material. As yet a further element of safety, even in the event such a vial were to break, the material will be wholly contained within the body 152 rendering handling for disposal easier and safer than procedures heretofor known or undertaken.

FIG. 16 shows a marker 160 placed on a patient undergoing radiological examination. The marker 160 is positioned at a specific location on the patient's body to provide a benchmark for measurement on the image resulting from the x-ray procedure. Thus, being radiopaque, a mark will appear either on an x-ray film or on a real time display permitting a physician to measure with reasonable precision the location of internal anatomy from that known point as evidenced by the marker. Such markers can also be used on inanimate objects for the same purpose. However, when associated with a human patient, the marker 160 may be used but a single time and then thrown away to avoid the transmission of bacteriological contamination to another patient.

FIG. 17A and 17B show film markers such as have been used in the past to identify x-ray films. In each case, the marker, identified generally as 170, is comprised of a support 172 bearing a letter indicia 174 either as an "R" or as an "L". These indicia are meant to identify radiographic representations as either the right or left part or extremity of some anatomical element or, if the object being examined is not a patient but an inanimate object, other markers of similar variety may be used to identify specific locations or characteristics. Typically, the support will be radio-transmissive whereas the indicia will be radiopaque. Where such markers are utilized with patients in x-ray examination and especially where the marker is placed in contact with the patient, the marker may then be disposed of. This is as opposed to the correct reuse of lead markers as reported above, such body contact having the tendency to transmit bacteriological contamination from patient to patient.

FIG. 18 is an illustration of an infant stabilization device including a protective radiological shield, designated generally as 180. The protective device includes a frame 182 having a plurality of straps or the like 184 for restraining the infant in position on the stabilization member. A border of radiation attenuating material, designated generally as 186, is disposed peripherally about the stabilization member while the infant may be provided with a diaper 187 likewise made from radiation attenuating material in accordance with the present invention. A cut-out region 188 is provided to allow x-ray examination of the infant or a selected portion of his anatomy. Typically, the infant is placed on the pad and is strapped into position with his hands suitably secured. With shielding in place, a holder such as the parent of the infant (also suitably protected) may assist in the x-ray procedure as required. In the course of that procedure, however, all individuals involved are shielded or otherwise protected. This is a major improvement over conventional boards used heretofore for this purpose; the pliable nature of the shielding adds both comfort and safety for the infant and the person supporting him during the x-ray procedure. The pliable nature adds comfort and safety to the infant vis-a-vis hard board.

FIGS. 19A, 19B and 19C illustrate different forms of patient positioning devices used in radiological procedures, either investigative or therapeutic. In FIG. 19A, a patient's hand is positioned on a positioning device 190; in FIG. 19B, the patient's leg is confined within a positioning device 192; and in FIG. 19C, the patient's head is suitably positioned within a device 194. In the past, foam rubber devices, sandbags, or similar articles were used to position a patient or restrain him from movement once an appropriate position was attained. Foam rubber tends to slide around, fails to provide any attenuation, and is generally uncomfortable. Typically, as well, such foam rubber positioners were reused. Following the principles described herein, a radiation attenuating material which is comfortable and reasonably adherent and comfortable to a patient's skin and the examining surface replaces the foam rubber previously used. Furthermore, to the extent necessary or desirable, radiation attenuation may be built into the positioning device.

FIG. 20 shows a fluoroscopic table pad 200. The table pad is of a generally rectilinear configuration, shaped as a web 202 fabricated from a one-quarter inch to one-half inch slab of radiation attenuating material in accordance with the present invention. Zones of neutral material 204 are formed in the pad 200, here disposed in shape and size as required for angiography which is the specific purpose for which this pad is constructed. Cutouts 206 in the pad allow items to be inserted through the pad as may be required. The pad is placed on the table beneath a patient undergoing angiography, during which he is subjected to x-ray radiation from beneath the table. The primary beam is allowed to pass through the pad only in the regions of the neutral material 204 and thus the patient is protected outside that zone where radiation is not necessary or desired.

FIG. 21 shows a pair of density wedges identified as 210. Each wedge is tapered and thus provide higher density radiopacity at the thicker edge than at the thinner or tapered edge. Such density wedges are oftentimes used in radiological procedures and these wedges find equal applicability where the same have been used in the past.

While the invention has now been disclosed with reference to certain preferred embodiments and exemplified with regard thereto, those skilled in the art will appreciate the various substitutions, modifications, omissions and changes may be made without departing from the spirit thereof. Accordingly, it is intended that the scope of the present invention be limited solely by the broadest interpretation accorded the appended claims.

What is claimed is:

1. A flexible shield for covering an article and attenuating the flux of electromagnetic radiation to or from said article, comprising a polymeric matrix charged with an attenuating filler; said shield having a transmission attenuation factor of at least 50% of a primary 100 kVp x-ray beam, a durometer of less than about 100 Shore "00" and a coefficient of sliding friction relative to said article of at least 0.15.

2. The shield of claim 1, wherein said transmission attenuation factor is at least 75%.

3. The shield of claim 1, wherein said transmission attenuation factor is at least 90%.

4. The shield of claim 1, wherein said transmission attenuation factor is at least 97%.

5. The shield of claims 1, 2, 3 or 4, wherein said shield has a scattering attenuation factor of at least 80%.

6. The shield of claim 5, wherein said scattering attenuation factor is at least 95%.

7. The shield of claim 5, wherein said scattering attenuation factor is at least 97%.

8. The shield of claim 1, wherein said durometer is in the range of from about 5 to about 80.

9. The shield of claim 1, wherein said durometer is in the range of from about 15 to about 40.

10. The shield of claim 1, wherein the coefficient of friction is greater than 0.5.

11. The shield of claim 1, wherein the coefficient of friction is greater than 0.75.

12. The shield of claim 1, wherein the coefficient of friction is greater than 1.0.

13. The shield of claim 1, wherein the coefficient of friction is greater than 2.0.

14. A flexible shield for shrouding an article and attenuating the flux of electromagnetic radiation to or from said article, comprising a viscoelastic polymeric matrix charged with an attenuating inorganic filler; said shield having a transmission attenuation factor of at least 90% and a scattering attenuation factor of at least 90% based on a 100 Kvp x-ray beam, a durometer in the range of from about 5 to about 80 Shore "00", and a coefficient of sliding friction relative to said article of at least 0.75.

15. The shield of claim 14, wherein said matrix is comprised of a polymer selected from the group consisting of viscoelastic vinyl polymers and copolymers, silicones and urethanes.

16. The shield of claim 15, wherein said filler is a particulate of an inorganic salt having a radiopaque cation.

17. The shield of claim 16, wherein said cation is selected from the group consisting of barium, bismuth, iodine, uranium, zirconium and mixtures thereof.

18. The shield of claim 17, wherein said matrix is a plasticized vinyl polymer and further wherein the ratio of plasticizer to polymer is in the range of from about 5:1 to about 32:1 and said filler is present in the range of up to about 50%.

19. The shield of claim 18, wherein said filler is present from about 10% to about 35%.

20. The shield of claim 19, wherein said filler is present from about 10% to about 20%.

21. A disposable radiological garment to be worn by or selectively draped about a patient, comprising a viscoelastic polymeric matrix charged with an attenuating inorganic filler, said garment having a durometer of less than 100 Shore "00".

22. The garment of claim 21, wherein said matrix exhibits elastic hysteresis over a strain range in excess of 150%.

23. The garment of claim 22, having a coefficient of sliding friction relative to said patient of at least 0.75.

24. The garment of claim 23, wherein said matrix is comprised of a vinyl polymer or copolymer and said filler is a barium compound.

25. The garment of claim 24, configured to envelop a selected anatomical region of said patient.

26. The garment of claim 24, configured to overlie a selected anatomical region of said patient.

27. The garment of claim 24, configured to underlie a selected anatomical region of said patient.

* * * * *